United States Patent [19]

Martin et al.

[11] 4,178,301

[45] Dec. 11, 1979

[54] BENZOIC ACID DERIVATIVES

[75] Inventors: Tellis A. Martin; William T. Comer, both of Evansville, Ind.

[73] Assignee: Mead Johnson & Company, Evansville, Ind.

[21] Appl. No.: 952,034

[22] Filed: Oct. 16, 1978

Related U.S. Application Data

[62] Division of Ser. No. 889,667, Mar. 24, 1978, Pat. No. 4,132,802, which is a division of Ser. No. 733,598, Oct. 18, 1976, Pat. No. 4,096,277, which is a division of Ser. No. 579,650, May 21, 1975, Pat. No. 4,005,222.

[51] Int. Cl.$^2$ ............................................. C07C 153/11
[52] U.S. Cl. ................................................. 260/455 R
[58] Field of Search ..................................... 260/455 R

[56] References Cited

U.S. PATENT DOCUMENTS

| | | | |
|---|---|---|---|
| 2,520,293 | 8/1950 | Weiss | 560/12 |
| 4,005,222 | 1/1977 | Martin et al. | 424/319 |
| 4,096,277 | 6/1978 | Martin et al. | 260/558 S |
| 4,132,802 | 1/1979 | Martin et al. | 424/303 |

*Primary Examiner*—John M. Ford
*Assistant Examiner*—Robert C. Whittenbaugh
*Attorney, Agent, or Firm*—Robert H. Uloth; Robert E. Carnahan

[57] ABSTRACT

A mucolytic process is disclosed which comprises contacting N-(2-hydroxyethyl)mercaptoacetamidobenzamides or mercaptoacylamidobenzoic acids, mercaptoacetylsulfanilic acids and alkanoylthio derivatives thereof with mucus. Illustrative of compounds useful in the mucolytic process of the present invention are 4-(2-mercaptoacetamido)benzoic acid and N-(2-mercaptoacetyl)sulfanilic acid.

1 Claim, No Drawings

BENZOIC ACID DERIVATIVES

CROSS REFERENCE TO RELATED APPLICATIONS

This application is a division of co-pending U.S. application Ser. No. 889,667, filed Mar. 24, 1978, now U.S. Pat. No. 4,132,802, which in turn is a division of U.S. application Ser. No. 733,598, filed Oct. 18, 1976, and now U.S. Pat. No. 4,096,277, which in turn is a division of U.S. application Ser. No. 579,650, filed May 21, 1975 and now U.S. Pat. No. 4,005,222.

BACKGROUND OF THE INVENTION

This invention deals with mucolytic agents and a process of the bio-affecting body treatment type. More particularly, the invention relates to a process for liquefying mucus adaptable for use in the treatment of mammals or for laboratory use.

A. L. Sheffner, Ann. N.Y. Acad. Sci., 106, 298–310 (1963), discloses that a variety of sulfhydryl containing compounds have mucolytic activity and, in an attempt to correlate mucolytic activity and chemical structure, stated that compounds having a free sulfhydryl group were generally effective in reducing mucus viscosity. None of the compounds disclosed by Sheffner were of the mercaptoacylamidobenzoic or sulfonic acid type. The subject matter of A. L. Sheffner U.S. Pat. No. 3,091,569 relates to N-acylated sulfhydryl compounds such as N-acetyl-L-cysteine which is commercially available under the trademark Mucomyst ® as a topically effective mucolytic agent. U. Weiss, U.S. Pat. No. 2,520,293 concerns mercaptoacetanilide derivatives and discloses antioxidant utility therefor. U.S. Pat. No. 3,809,697 issued to Martin and Comer, the inventors of the instant invention, disclose a group of 1,4-bis-acyl-piperazines having mucolytic properties.

It has now been found surprisingly that mercaptoacylamidobenzoic acids disclosed in Weiss, U.S. Pat. No. 2,520,293 and N-(2-mercaptoacetyl)sulfanilic acids are topically effective mucolytic agents substantially more potent than N-acetyl-L-cysteine.

SUMMARY OF THE INVENTION

This invention relates to a process for liquefying mucus which comprises contacting the mucus with an effective mucolytic amount of a compound characterized by Formula I.

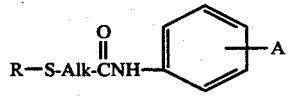

Formula I

In Formula I, A is meta or para oriented with respect to the

radical and is selected from the group consisting of carboxylic, sulfonic and N-(2-hydroxyethyl)carboxamide radicals represented by the symbols $CO_2H$, $SO_3H$, $CONHCH_2CH_2OH$, respectively. The symbol "Alk" comprehends a divalent alkylene radical joining "S" and "CO" and contains from one to three carbon atoms inclusive such as methylene ($-CH_2-$), ethylene ($-CH_2CH_2-$), propylene ($-CH_2CH_2CH_2-$), ethylidene

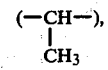

1,2-propylene

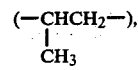

isopropylidene

R represents hydrogen whenever the "A" substitutent is carboxylic, sulfonic, or N-(2-hydroxyethyl)carboxamide. In addition, whenever A is carboxylic or sulfonic, R can also be alkanoyl having up to eighteen carbon atoms inclusive. The salts of those substances wherein "A" is carboxylic or sulfonic are also part of the present invention. The preferred salts are those prepared from pharmaceutically acceptable alkali metals such as sodium, potassium, calcium and bases such as ammonia. "Pharmaceutically acceptable" as used herein to describe the alkali metal and ammonium salts refers to those cationic species which do not contribute appreciably to the toxicity of the product nor to its pharmacological activity.

A particularly preferred group of compounds useful as mucolytic agents comprises those of Formula I wherein Alk is methylene, R is hydrogen or acetyl, and A is carboxylic or sulfonic.

A still further preferred group of compounds comprises those substances of Formula I wherein R is limited to hydrogen, Alk is methylene, and A is carboxylic, sulfonic or N-(2-hydroxyethyl)-carboxamide.

Particularly preferred specific compounds included within the scope of this invention are
N-(2-mercaptoacetyl)sulfanilic acid,
4-(2-mercaptoacetamido)benzoic acid,
3-(2-mercaptoacetamido)benzoic acid,
N-(2-hydroxyethyl)-4-(2-mercaptoacetamido)benzamide and
4-[2-(acetylthio)acetamido]benzoic acid.

Some of the aforementioned compounds are known to the art and are reported to be of value for non-medical related utilities. Both 4-(2-mercaptoacetamido)benzoic acid and 3-(2-mercaptoacetamido)-benzoic acid are described in U.S. Pat. No. 2,520,293 as antioxidants while the sodium salt of N-(2-mercaptoacetyl)sulfanilic acid has been described by N. S. Poonia, et al., Indian J. Appl. Chem., 27 (1) 32–33 (1964) as a reagent for the colorimetric determination of potassium.

Those compounds of Formula I wherein A is carboxyl or sulfonic may be partially or completely neutralized by adjusting the pH of a solution to be used in the mucolytic process of the present invention. The pH adjustment is carried out by addition of suitable alkaline reacting substances such as sodium hydroxide, ammonium hydroxide, potassium hydroxide, calcium hydroxide and the like. Salts of this type are considered biologically equivalent to the parent acid with respect to mucolytic activity. When a molar equivalent of an alkaline base is employed, the alkaline salt form thus obtained can be recovered according to conventional techniques such as evaporation, lyophylization or precipitation with a suitable solvent. For instance, addition of 1 N sodium hydroxide to a suspension of 4-(mercaptoacetamido)benzoic acid in isopropanol-water under an atmosphere of nitrogen affords sodium 4-(mercaptoacetamido)benzoate by addition of isopropanol and cooling. Ammonium 4(mercaptoacetamido)-benzoate and calcium 4-(mercaptoacetamido)benzoate further illustrate pharmaceutically acceptable salts of the compounds of Formula I.

Compounds of Formula I are synthesized by conventional methods adaptable for preparation of mercaptans and thio esters. For instance, U.S. Pat. No. 2,520,293 discloses preparation of 4-(2-mercaptoacetamido)benzoic acid by basic hydrolysis of N-α-(carbamylmercaptoacetyl)-p-aminobenzoic acid. This method is applicable to preparation of compounds of Formula I, wherein R is hydrogen and A is carboxylic.

A preferred process for preparing compounds of the present invention characterized by Formula I comprises reacting a compound of Formula II

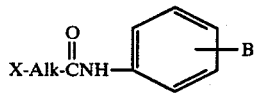

Formula II wherein Alk is as defined above, X is halogen such as bromine, iodine or chlorine, B is meta or para $CO_2H$, $CO_2R_2$ wherein $R_2$ is lower alkyl of 1 to 4 carbon atoms inclusive, $SO_3H$ or $CONHCH_2CH_2OH$ with an alkali metal salt (e.g., sodium or potassium) of a thiol of the formula $R_1$-SH wherein $R_1$ is alkanoyl of 1 to 18 carbon atoms inclusive to provide alkanoyl compounds of Formula III

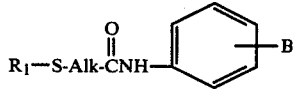

Formula III wherein $R_1$, Alk and B are as above defined and thereafter, if desired, hydrolyzing said alkanoyl compounds to provide the compounds of Formula I wherein R is hydrogen.

Hydrolysis of the compounds of Formula III may be carried out according to conventional techniques by interaction with an alkoxide such as sodium or potassium methoxide or a base such as sodium or potassium hydroxide in a reaction inert solvent such as methanol, ethanol, water, dimethylformamide, and the like. The resultant products have acid character and are isolated by first neutralizing the reaction mixture with an acid, such as acetic or hydrochloric and, then removing the solvent.

In carrying out the reaction of the alkali metal salts of

with the halogen intermediates of Formula II having a free carboxylic or sulfonic acid group, the acid function is neutralized by addition of an alkali metal hydroxide such as potassium or sodium hydroxide before reacting with the thiol.

It will be recognized by those skilled in the art that the mucolytic process of the present invention may be practiced in vivo as well as in vitro. The in vivo process is employed where it is desirable or necessary to liquefy mucus produced as a result of pathological conditions involving mucus producing tissue, particularly for example congestion of the respiratory system, vaginal tract and the like. The in vitro process is employed where it is desirable to reduce viscosity of mucus in order to facilitate analytical determinations or other examination. For instance, the compounds of Formula I can be used as sputum digestants in the isolation of mycobacteria. The concentration in which the compounds of Formula I have been found to effectively induce liquefaction of mucus is between about 0.003 to 0.5 molar. In carrying out the in vitro mucolytic process of the present invention, an aqueous solution or suspension of a compound of Formula I is prepared at the desired concentration and then mixed with mucus at a ratio of about 0.2 ml. of the solution or suspension of the mucolytic agent to each 1.0 ml. of mucus. Generally, satisfactory liquefaction of the mucus will be obtained within the period of about 1 to 15 minutes. It is to be understood that in addition to pharmaceutically acceptable salts of the compounds characterized by Formula I, other suitable cationic species can be employed in the in vitro process which would be generally precluded in the in vivo process because of excessive toxicity.

In accordance with the in vivo process of the present invention, the compounds of Formula I are administered in an amount sufficient to induce liquefaction of mucus in the respiratory tract of mammals in need thereof. Intratracheal administration of the compounds of Formula I is effected by various inhalation or instillation means such as by nose drops, sprays, aerosols, and the like. Another suitable means of administration is by insufflation of micronized particles or ultra-fine powder utilizing only the energy of the inspiratory action or by use of aerosol propellants. Solutions or suspensions having about 0.5 to 5% by weight of the mucolytic agent of Formula I are suitable for application by spraying with an atomizer, nebulizer, aerosol and the like.

It will be readily apparent to those skilled in the medical arts, that the correct dosage of a compound of Formula I to be employed with any particular mammalian subject is determined by the severity of the condition requiring mucolytic therapy, as well as the age, sex, weight, and general physical condition of the subject. Individual doses ranging from 5-100 mg. for inhalation by man are suitable and may be repeated as required for the desired mucolytic effect.

The substances of Formula I are relatively non-toxic substances substantially free of other pharmacologic action. 4-(2-Mercaptoacetamido)benzoic acid, a representative compound of Formula I, has an approximate oral $LD_{50}$ of 2000 mg./kg. body weight and an approximate $TD_{50}$ of 250 mg./kg. body weight in the mouse. When given intraperitoneally this compound has an $LD_{50}$ of 1108 mg./kg. body weight.

The following examples are only intended to illustrate the present invention and are not to be construed as limiting the invention in any respect.

EXAMPLES OF SPECIFIC EMBODIMENTS

EXAMPLE 1

Mucolytic Activity of Representative Compounds of Formula I.

Mucolytic activity was determined using the method of J. Lieberman, Am. J. Resp. Dis., 97, 662 (1968). This is a viscometric method which employs a cone-plate viscometer (Brookfield Engineering Laboratories, Inc., Stoughton, Mass.). According to this method, a 2 ml. aliquot of a batch of purulent human sputum (obtained from bronchitic patients) is transferred to the center of the viscometer plate and the temperature is allowed to equilibrate. The plate is then rotated at gradually increasing speeds up to 100 r.p.m. during a two-minute period. This reduces the amount of sputum on the test plate to 1 ml. and reduces the viscosity of the specimen to a reproducible value which is necessary because of the thixotropic properties of sputum. The rotation is then reduced to give a convenient reading on the instrument and a solution of the test drug having a volume of 0.2 ml. is then added to the sputum cup and readings as percent reduction in viscosity of the original are recorded at time intervals of one to three minutes for a period of 15 min. The test is repeated with N-acetyl-L-cysteine employing another aliquot of sputum to establish a control for comparison purposes. Relative molar potencies compared to N-acetyl-L-cysteine (NAC) can be determined by varying concentration of the test agent until approximately equivalent mucolytic activity is obtained. Results of this test for representative compounds of Formula I are given below.

TABLE I

MUCOLYTIC ACTION - PERCENT REDUCTION IN VISCOSITY
Compound 1. - 4-(2-MERCAPTOACETAMIDO)BENZOIC ACID

| Time (min.) | NAC 0.06 Molar | Compound 1 0.01 Molar | Compound 1 0.005 Molar |
|---|---|---|---|
| 1 | 36 | 45 | 32 |
| 3 | 45 | 63 | 50 |
| 6 | 52 | 69 | 57 |
| 9 | 50 | 76 | 55 |
| 12 | 52 | 82 | 55 |
| 15 | 60 | 84 | 55 |

On a molar basis, Compound 1 is approximately 12 times as active as N-acetyl-L-cysteine.

TABLE II

MUCOLYTIC ACTION - PERCENT REDUCTION IN VISCOSITY
Compound 2. - 3-(2-MERCAPTOACETAMIDO)BENZOIC ACID

| Time (min.) | NAC 0.03 Molar | Compound 2 0.03 Molar |
|---|---|---|
| 1 | 33 | 44 |
| 3 | 34 | 67 |
| 6 | 36 | 81 |
| 9 | 34 | 89 |
| 12 | 34 | 91 |
| 15 | 34 | 93 |

On a molar basis, Compound 2 is substantially more active than N-acetyl-L-cysteine.

TABLE III

MUCOLYTIC ACTION - PERCENT REDUCTION IN VISCOSITY
Compound 3. - N-(2-MERCAPTOACETYL)SULFANILIC ACID

| Time (min.) | NAC 0.06 Molar | Compound 3 0.01 Molar | Compound 3 0.005 Molar |
|---|---|---|---|
| 1 | 36 | 46 | 34 |
| 3 | 45 | 64 | 47 |
| 6 | 52 | 66 | 50 |
| 9 | 50 | 68 | 50 |
| 12 | 52 | 77 | 47 |
| 15 | 60 | 82 | 44 |

On a molar basis, Compound 3 is approximately 10 to 12 times as active as N-acetyl-L-cysteine.

TABLE IV

MUCOLYTIC ACTION - PERCENT REDUCTION IN VISCOSITY
Compound 4. - N-(2-HYDROXYETHYL)-4-(2-MERCAPTOACETAMIDO)BENZAMIDE

| Time (min.) | NAC 0.03 Molar | Compound 4 0.005 Molar | Compound 4 0.002 Molar | Compound 4 0.001 Molar |
|---|---|---|---|---|
| 1 | 25 | 30 | 26 | 25 |
| 3 | 32 | 58 | 37 | 32 |
| 6 | 40 | 67 | 42 | 36 |
| 9 | 42 | 75 | 44 | 36 |
| 12 | 42 | 82 | 44 | 36 |
| 15 | 40 | 82 | 42 | 34 |

On a molar basis, Compound 4 is approximately 15 times as active as N-acetyl-L-cysteine.

TABLE V

MUCOLYTIC ACTION - PERCENT REDUCTION IN VISCOSITY
Compound 5. - 4-[2-(ACETYLTHIO)ACETAMIDO]BENZOIC ACID

| Time (min.) | NAC 0.03 Molar | Compound 5 0.03 Molar |
|---|---|---|
| 1 | 29 | 34 |
| 3 | 33 | 42 |
| 6 | 40 | 54 |
| 9 | 40 | 54 |
| 12 | 43 | 52 |
| 15 | 40 | 48 |

On a molar basis, Compound 5 is significantly more active than N-acetyl-L-cysteine.

EXAMPLE 2

In order that the compounds of Formula I should be readily available to those persons desiring to practice the mucolytic process of the present invention, the following synthetic procedures are given. The compound number corresponds to the number of those substances of Formula I listed hereinabove in Tables I–V.

Compound 1

To a mixture of methyl 4-[2-(acetylthio)-acetamido]-benzoate (15 g., 0.056 mole) in 100 ml. of ethanol is added 72 ml. (0.18 mole) of 10% sodium hydroxide. The reaction mixture is stirred for a period of 16 hr. at room temperature and then acidified with 32 ml. of 6 N hydrochloric acid to provide an off white solid which is collected, washed with water and dried yielding 11.2 g., (95% yield) of the mercaptobenzoic acid product. Crystallization of the solid from ethanol employing decolorizing charcoal affords analytically pure 4-(2-MERCAP- TOACETAMIDO)BENZOIC ACID, m.p. 232.0°–233.0° C. (dec.) (corr).

Analysis. Calcd. for $C_9H_9NO_3S$: C, 51.17; H, 4.29; N, 6.63. Found: C, 51.26; H 4.34; N, 6.49.

By substituting an equimolar amount of
methyl 4-[2-(acetylthio)propionamido]benzoate or
methyl 4-[3-(acetylthio)propionamido]benzoate
for methyl 4-[2-(acetylthio)acetamido]benzoate in the procedure of Compound 1, there is provided, respectively
4-(2-MERCAPTOPROPIONAMIDO)BENZOIC ACID and
4-(3-MERCAPTOPROPIONAMIDO)BENZOIC ACID.

Compound 2

To a mixture of methyl 3-[2-(acetylthio)-acetamido]-benzoate (15 g., 0.056 mole) in 100 ml. of ethanol is added 72 ml. (0.18 mole) of 10% sodium hydroxide solution over a period of 10 minutes. The reaction mixture is stirred for a period of 16 hr. and acidified with 6 N hydrochloric acid to provide a solid which is collected, washed with water and dried, yielding 11.5 g., (97% yield) of the mercaptobenzoic acid product as a white solid. Crystallization of the solid from anhydrous ethanol affords analytically pure 3-(2-MERCAPTOACETAMIDO)BENZOIC ACID, m.p. 217.0°–219.0° C.

Analysis. Calcd. for $C_9H_9NO_3S$: C, 51.17; H, 4.29; N, 6.63. Found: C, 51.15; H, 4.41; N, 6.42.

Compound 3

To a slurry of N-[2-(acetylthio)acetyl]sulfanilic acid potassium salt (6.5 g., 0.02 mole) in 50 ml. of methanol is added dropwise 4 ml. (0.04 mole) of 10 N potassium hydroxide while maintaining a temperature of 25°–30° C. The reaction mixture is stirred for 3 hr. during which time a solution is obtained. Acetic acid (1.5 ml., 0.025 mole) is then slowly added to the reaction mixture to provide a white solid which is collected, washed with methanol and dried affording 5.4 g. (95% yield) of analytically pure N-(2-MERCAPTOACETYL)SULFANILIC ACID POTASSIUM SALT, m.p. 335.0°–336.0° C. (dec.) (corr.).

Analysis. Calcd. for $C_8H_8NO_4S_2.K$: C, 33.67; H, 2.83; N, 4.91. Found: C, 33.45; H, 2.88; N, 4.74.

By substituting the sodium salt of N-[2-(acetylthio)acetyl]-sulfanilic acid and sodium hydroxide in place of the potassium salt and potassium hydroxide, respectively, according to the above procedure, there is provided N-(2-MERCAPTOACETYL)SULFANILIC ACID SODIUM SALT.

By substituting an equimolar amount of 3-[2-(acetylthio)-acetamido]benzensulfonic acid potassium salt or 4-[2-(acetylthio)-propionamido]benzenesulfonic acid potassium salt or 4-[3-(acetylthio)-propionamido]benzenesulfonic acid potassium salt, respectively, for N-[2-(acetylthio)acetyl]sulfanilic acid potassium salt in the procedure of Compound 3, there is provided
3-(2-MERCAPTOACETAMIDO)BENZENESULFONIC ACID POTASSIUM SALT,
4-(2-MERCAPTOPROPIONAMIDO)BENZENESULFONIC ACID POTASSIUM SALT, and
4-(3-MERCAPTOPROPIONAMIDO)BENZENESULFONIC ACID POTASSIUM SALT.

Compound 4

To a mixture of 4-[2(acetylthio)acetamido]-N-(2-hydroxyethyl)benzamide (19.5 g., 0.066 mole) in 200 ml. of methanol is added 13.4 ml. (0.134 mole) of a 40% solution of sodium hydroxide over a period of 5 minutes. After stirring for 1 hr., the mixture is acidified with 23 ml. (0.138 mole) of 6 N hydrochloric acid, filtered and the filtrate diluted with 125 ml. of water. After cooling the reaction mixture at acetone-dry ice bath temperature, the precipitate which forms is collected, washed with 50% ethanol and dried affording 14 g. (83% yield) of product. Crystallization of this material from ethanol provides analytically pure N-(2-HYDROXYETHYL)-4-(2-MERCAPTOACETAMIDO)BENZAMIDE, m.p. 184.0°–186.0° C. (corr.).

Analysis. Calcd. for $C_{11}H_{14}N_2O_3S$: C, 51.95; H, 5.55; N, 11.01. Found: C, 51.74; H, 5.47; N, 10.81.

Compound 5

To a suspension of 4-(2-chloroacetamido)-benzoic acid (6.4 g., 0.03 mole) in 75 ml. of water is added slowly 30 ml. (0.03 mole) of 1 N potassium hydroxide while maintaining a temperature of 10° C. When the addition is complete, potassium thiolacetate (3.5 g., 0.06 mole) is added at 25° C., and the reaction mixture then stirred for a period of 16 hr. and filtered. Acidification of the filtrate with hydrochloric acid provides an 87% yield of product. Crystallization of this material from ethanol affords analytically pure 4-[2-(ACETYLTHIO)ACETAMIDO]BENZOIC ACID, m.p. 233°–234° C.

Analysis. Calcd. for $C_{11}H_{11}NO_4S$: C, 52.16; H, 4.38; N, 5.53; S, 12.66. Found: C, 52.20; H, 4.34; N, 5.44; S, 12.40.

By substituting equimolar amounts of 4-(2-chloropropionamido)-benzoic acid or 4-(3-chloropropionamido)-benzoic acid for 4-(2-chloroacetamido)benzoic acid in the procedure of Compound 5 there is provided, respectively
4-[2-(ACETYLTHIO)PROPIONAMIDO]BENZOIC ACID and
4-[3-(ACETYLTHIO)PROPIONAMIDO]BENZOIC ACID.

By substituting equimolar amounts of the potassium salt of
thiolpropionic acid,
thioloctanoic acid,
thiolhexadecanoic acid,
thiolisobutyric acid,
respectively, for potassium thiolacetate in the procedure of Compound 5 there is provided, respectively
4-[2-(PROPIONYLTHIO)ACETAMIDO]BENZOIC ACID,
4-[2-(OCTANOYLTHIO)ACETAMIDO]BENZOIC ACID,
4-[2-(HEXADECANOYLTHIO)ACETAMIDO]BENZOIC ACID, and
4-[2-(ISOBUTYROYLTHIO)ACETAMIDO]BENZOIC ACID.

Compound 6

A mixture of methyl 4-(2-chloroacetamido)-benzoate (4.2 g., 0.0184 mole) and potassium thiolacetate (2.2 g., 0.019 mole) in 75 ml. of acetone is refluxed for 16 hr., filtered and the filtrate concentrated under reduced pressure. The residual solid thus obtained is dissolved in ethyl acetate, treated with decolorizing charcoal and then diluted with n-hexane to afford an 81% yield of crude acetylthioester. Crystallization of the crude product from ethyl acetate-n-hexane affords analytically pure METHYL 4-[2-(ACETYLTHIO)ACETAMIDO]BENZOATE, m.p. 137.0°–139.0° C. (corr.).

Analysis. Calcd. for $C_{12}H_{13}NO_4S$: C, 53.92; H, 4.90; N, 5.24. Found: C, 53.98; H, 4.92; N, 5.03.

Compound 7

A mixture of methyl 3-(2-chloroacetamido)-benzoate (16 g., 0.07 mole) and potassium thiolacetate (7.1 g., 0.065 mole) in 150 ml. of acetone is refluxed for 4.5 hr. After cooling, the reaction mixture is filtered and the filtrate concentrated under reduced pressure. The residual solid thus obtained is slurried with n-hexane to afford an 86% yield of crude product. Crystallization of the crude product from ethyl acetate-n-hexane affords analytically pure METHYL 3-[2-(ACETYLTHIO)ACETAMIDO]BENZOATE, m.p. 117.5°–119.5° C.

Analysis. Calcd. for $C_{12}H_{13}NO_4S$: C, 53.92; H, 4.90; N, 5.24. Found: C, 53.98; H, 5.02; N, 4.89.

Compound 8

A mixture of 4-(2-chloroacetamido)-N-(2-hydroxyethyl)benzamide (39.3 g., 0.153 mole) and potassium thiolacetate (18.3 g., 0.16 mole) in 650 ml. of acetone is heated at reflux temperature for a period of 2 hr. After standing overnight, the reaction mixture is filtered, the filtercake washed with acetone, slurried with water, filtered and the filtercake washed with water and dried to afford 34.7 g. of crude product. Crystallization of this material from ethyl acetate-methanol affords analytically pure 4-[2-(ACETYLTHIO)ACETAMIDO]-N-(2-HYDROXYETHYL)BENZAMIDE, m.p. 190.0°–192.0° C. (corr.) in 57% yield.

Analysis. Calcd. for $C_{13}H_{16}N_2O_4S$: C, 52.69; H, 5.44; N, 9.45. Found: C, 52.64; H, 5.40; N, 9.18.

Compound 9

A mixture of N-(2-chloroacetyl)sulfanilic acid potassium salt (21 g., 0.073 mole) and potassium thiolacetate (8.8 g., 0.077 mole) in 100 ml. of dimethylformamide is stirred for a period of 3 hr. while maintaining a temperature of 50°–55° C. After standing for a period of 16 hr., the reaction mixture is filtered and the filter cake washed with dilute ethanol. The crude acetylthio compound thus obtained is first crystallized from water, and then from water-ethanol using activated charcoal to provide analytically pure N-[2-(ACETYLTHIO)ACETYL]SULFANILIC ACID POTASSIUM SALT as a white solid, m.p. >320.0° C.

Analysis. Calcd. for $C_{10}H_{10}NO_5S_2 \cdot K$: C, 36.68; H, 3.08; N, 4.28. Found: C, 37.00; H, 3.23; N, 4.16.

EXAMPLE 3—Inhalation Compositions

A. Powder For Administration via Inhaler Device 4-(2-mercaptoacetamido)benzoic acid, micronized: 2.5 g.

Lactose powder: 2.5 g.

The powders are blended asceptically and filled into hard gelatin capsules each containing 50 mg. of the mixture. This is suitable for dispersion into the inspired breath by means of a breath-operated inhaler device containing means for rupture of the capsule wall prior to dosing.

B. Pressured Aerosol Dispersion For Delivery of a Powder 4-(2-mercaptoacetamido)benzoic acid, micronized: 6.25 g.

Oleyl Alcohol: 0.1 g.

Dichlorodifluoromethane: 25.0 g.

Dichlorotetrafluoroethane: 68.65 g.

The micronized drug is dispersed in a solution of the other ingredients which has been cooled to −20° C. and filled into a chilled aerosol container having a metered valve arranged to deliver 80 mg. of the composition at a single dose. This dose contains 5 mg. of active ingredient.

C. Lyophilized Powder for Reconstitution.

A solution of 1 g. disodium edeate, 10 g. of 4-(2-mercaptoacetamido)benzoic acid and 90 g. of mannitol in 4 l. of water that is adjusted to pH 5.5 with sodium hydroxide solution is sub-divided equally into 1000 ampoules. The ampoules are frozen and the frozen mixture lyophilized to dryness. The ampoules are then sealed or capped. For use, each ampoule is reconstituted with 4 ml. of a solution having the following composition.

Sodium chloride, 0.4% w/w

Sodium hydroxide or hydrochloric acid, q.s.: pH 6.5

Purified water, q.s: 4.0 ml.

D. Sterile Lyophilized Powder

A solution of 20 g. of 4-(2-mercaptoacetamido)benzoic acid and 20 g. of polyvinylpyrrolidone C-30 (average molecular weight about 40,000) is dissolved in 8 l. of water, sub-divided into 1000 sterile glass vials using a sterilizing filter and aseptically lyophilized to dryness. The vials are aseptically bacterial sealed. A suitable solvent for reconstitution of the sterile powder is sterile aqueous 0.9% sodium chloride in purified water adjusted to pH 6.5. A 20 mg. dose of the composition is reconstituted with 4 ml. of this vehicle before use.

E. Sterile Solution 4-(2-mercaptoacetamido)benzoic acid: 10.0 g.

Disodium edetate: 0.5 g.

Sodium hydroxide to pH 6.5

Purified, distilled and deoxygenated water, q.s.: 1000 ml.

The above solution is prepared under a nitrogen atmosphere and aseptically filled into sterile ampoules using a sterilizing filter. The filled ampoules are immediately flushed with sterile nitrogen and flame sealed.

Composition C and D may be administered by a conventional nebulizing apparatus or by an intermittent pressure breathing apparatus. An equal weight of a pharmaceutically acceptable salt of 4-(2-mercaptoacetamido)benzoic acid may be substituted for the free acid in Compositions A through E, if desired.

What is claimed is:

1. 4-[2-(Acetylthio)acetamido]benzoic acid.

* * * * *